(12) United States Patent
Vicatos et al.

(10) Patent No.: US 9,308,089 B2
(45) Date of Patent: Apr. 12, 2016

(54) ENDOPROSTHESIS

(75) Inventors: George Vicatos, Cape Town (ZA); Samuel Isaac Ginsberg, Milnerton (ZA); Adam Thane Parsons, Wynberg (ZA)

(73) Assignee: University of Cape Town, Cape Town (ZA)

( * ) Notice: Subject to any disclaimer, the term of this patent is extended or adjusted under 35 U.S.C. 154(b) by 104 days.

(21) Appl. No.: 14/127,933

(22) PCT Filed: Jun. 27, 2012

(86) PCT No.: PCT/IB2012/053247
§ 371 (c)(1),
(2), (4) Date: Mar. 13, 2014

(87) PCT Pub. No.: WO2013/001463
PCT Pub. Date: Jan. 3, 2013

(65) Prior Publication Data
US 2014/0236311 A1      Aug. 21, 2014

(30) Foreign Application Priority Data

Jun. 27, 2011   (ZA) .................................. 2011/04740

(51) Int. Cl.
*A61F 2/28*     (2006.01)
*A61B 17/72*    (2006.01)
*A61F 2/30*     (2006.01)
*A61B 19/00*    (2006.01)
*A61B 17/00*    (2006.01)
*A61F 2/48*     (2006.01)

(52) U.S. Cl.
CPC ............... *A61F 2/28* (2013.01); *A61B 17/7216* (2013.01); *A61B 19/46* (2013.01); *A61B 2017/00017* (2013.01); *A61F 2002/30551* (2013.01); *A61F 2002/30706* (2013.01); *A61F 2002/482* (2013.01); *A61F 2002/488* (2013.01); *A61F 2250/0001* (2013.01)

(58) Field of Classification Search
None
See application file for complete search history.

(56) References Cited

U.S. PATENT DOCUMENTS

| 5,626,579 A | 5/1997 | Muschler et al. |
| 7,753,915 B1 | 7/2010 | Eksler et al. |
| 2006/0069447 A1* | 3/2006 | DiSilvestro et al. ....... 623/23.16 |

FOREIGN PATENT DOCUMENTS

| EP | 1642550 A2 | 4/2006 |
| WO | WO 2010/050890 A1 | 5/2010 |

* cited by examiner

*Primary Examiner* — David H Willse
(74) *Attorney, Agent, or Firm* — Bret E. Field; Bozicevic, Field & Francis LLP

(57) ABSTRACT

An endoprosthesis is proved which includes an elongate housing having a drive secured through a threaded drive shaft to an extension shaft therein, the drive operable to cause the extension shaft to move axially with respect to the body, and the extension shaft and housing configured to be securable to a bone to act as a prosthetic replacement for removed bone. An operating system for the endoprosthesis is also provided.

8 Claims, 6 Drawing Sheets

ENDOPROSTHESIS

FIELD OF THE INVENTION

This invention relates to an endoprosthetic device for use in replacing and extending human limbs, particularly, but not exclusively, in skeletally immature patients.

BACKGROUND TO THE INVENTION

Osteosarcoma occurs in the region of the bone (the ends) where cells are actively replicating resulting in growth and lengthening of the bone. The presence of cancer necessitates the surgical removal of the cancerous bone, typically involving the joint, preventing further growth in this region. Limb salvage surgery is often performed in such cases and requires the use of an extension device which serves as a prosthetic replacement for the removed bone as well as allowing for extension, mimicking normal growth. It is also applied in, for example, patients with trauma wounds such as may be caused by gunshots, accidents and explosive devices.

There are very few devices that perform limb lengthening. These devices need minimal surgical procedures to lengthen. More recent devices obviate the need for surgery to lengthen. Only recently, motorised devices were introduced into the market, but these utilise permanent magnets internal to the device and cumbersome and heavy external induction coils to operate the motors. Also, microcontrollers are used to control operation of the motor to ensure precise incremental extension is achieved. These, however, limit the type of sterilisation that can be performed on the endoprosthesis and patient imaging or diagnostic methods that can be used to those which entail minimal or no radiation as radiation causes the contents of many memory types to be damaged. This includes the Flash and EEPROM used to store programs in the vast majority of microcontroller devices. Furthermore, these microcontrollers rely on measurements made by sensors placed on the devices to control the operation of the motor to achieve a desired extension.

SUMMARY OF THE INVENTION

According to the invention there is provided an endoprosthesis which includes an elongate housing having a drive secured through a threaded drive shaft to an extension shaft therein, the drive operable to cause the extension shaft to move axially with respect to the housing and the extension shaft and housing configured to be securable to a bone to act as a prosthetic replacement for removed bone, and for the drive to be operable through a control circuit which includes an inductive coil, characterised in that the control circuit is configured to provide a predetermined output which operates the drive in a step-wise fashion upon receiving power through the inductive coil.

Further features of the invention provide for the control circuit to be configured through hardwiring; for the drive to include a motor, preferably a piezoelectric motor, and gearbox; and for the drive, drive shaft and extension shaft to be substantially co-axially arranged.

Still further features of the invention provide for the control circuit to include a number of cascaded circuits, each of which provides an output which drives one phase of the motor; and for the cascaded circuits to each include a time delay.

Yet further features of the invention provide for one or more strain gauges to be secured to parts of the endoprosthesis to measure strain of those parts and to transmit such information through the skin using radio techniques or by using coded patterns of current impulses through the inductive coil.

The invention also provides an operating system for an endoprosthesis as defined above comprising an external operating unit which supplies an alternating magnetic field to the internal inductive coil and which is controlled by a processor, preferably a microcontroller, which is configured to cause operation of the motor, through the inductive coil, to achieve a required extension of the endoprosthesis by measuring rotation of the motor through feedback received from the inductive coil.

Further features of the invention provide for the feedback to be received from analysis of the current through or voltage across the inductive coil; for the external operating unit to be connectable to a computer to receive extension parameters which provide required extensions over a period of time, and to transmit operating information; and for the external operating unit to include an RFID reader to identify that the external operating unit is being applied to the correct endoprosthetic device by reading an RFID tag associated with the endoprosthesis.

DETAILED DESCRIPTION WITH REFERENCE TO THE DRAWINGS

Figure 1:
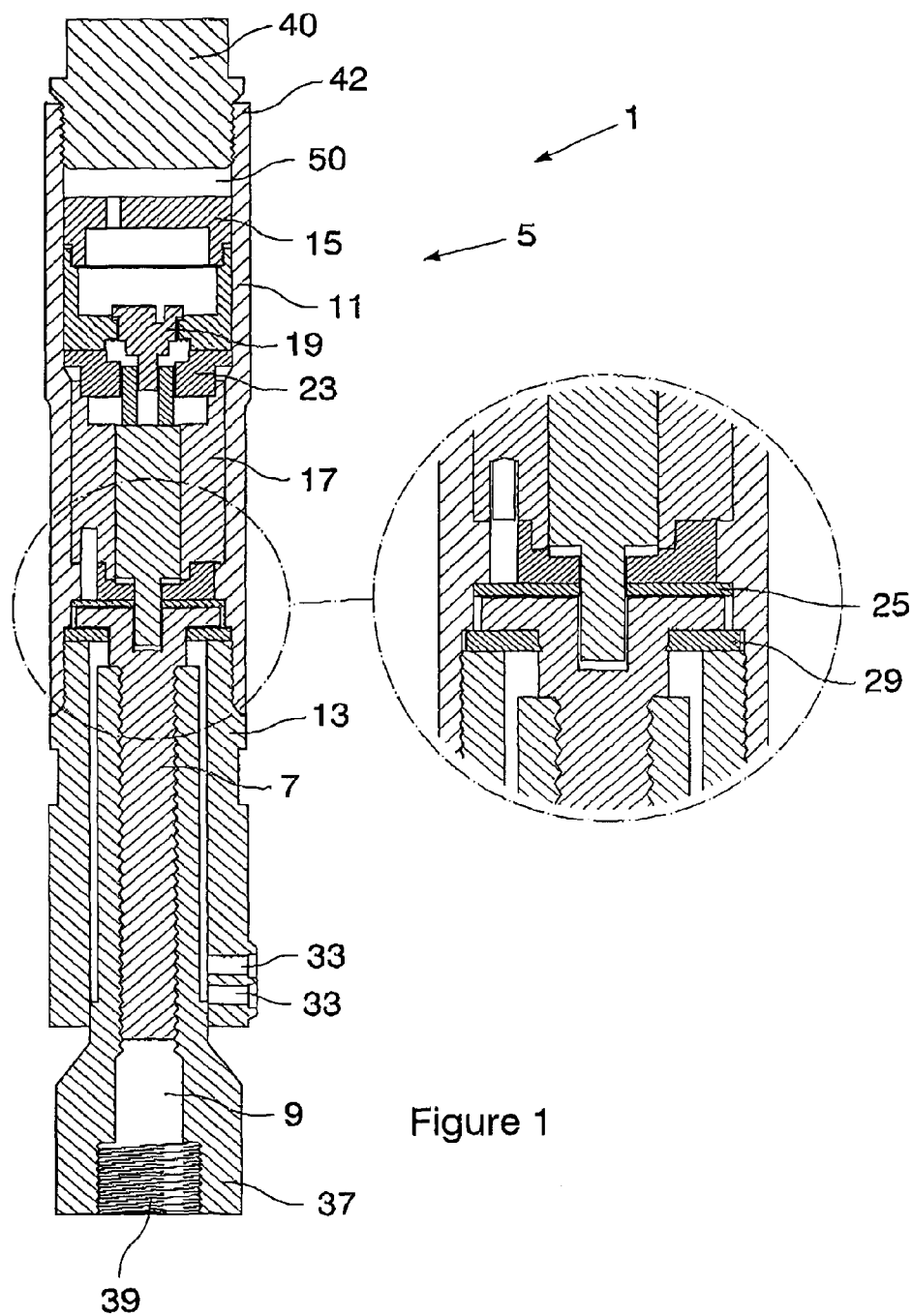
FIG. 1 is a sectional elevation of an endoprosthesis.
Figure 2:
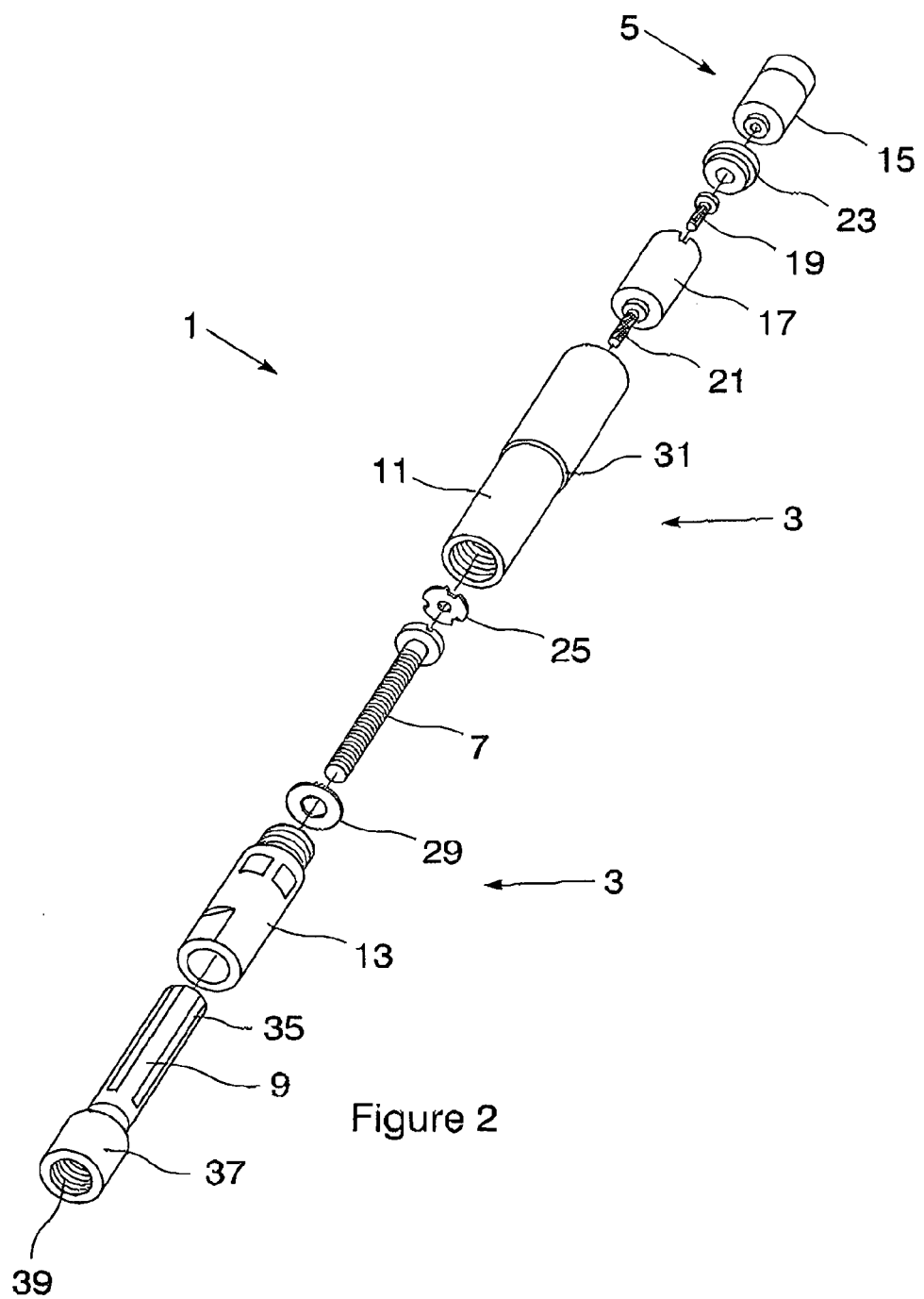
FIG. 2 is an exploded perspective view of the endoprosthesis in FIG. 1.

An endoprosthesis (1) which can be used to provide linear extension of long bones in vivo for skeletally immature patients is shown in FIGS. 1 and 2 and includes an elongate, tubular housing (3) in which are located a drive (5) secured through a threaded drive shaft (7) to and extension shaft (9) in coaxial alignment.

The housing (3) is of two-part construction providing drive casing (11) and shaft cover (13) in screw threaded engagement with each other.

The drive (5) includes a piezoelectric motor (15) connected to a gearbox (17) through a transition shaft (19). The gearbox output shaft (21) has a hexagonal shape and provides a complementary fit within a socket in the end of the drive shaft (7).

The gearbox and motor are rigidly fixed to one another, in this embodiment by means of an adapter plate (23) and mounting screws.

The drive (5) is rigidly secured within the drive casing (11) by three machine screws. A polished spacing plate (25) provides clearance between the screw heads and the drive shaft (7), as well as a low friction contact surface for the rotating drive shaft (7). The drive shaft (7) locates within the drive casing (11) on the gearbox output shaft (21) and against the spacing plate (25).

An ultra-high molecular weight polyethylene (UHMWPE) seal (29) locates on the drive shaft (7) against a shoulder (31) within the drive casing (11). The liquid seal with the drive shaft is produced by an interference fit.

The shaft cover (13) threads into the drive casing (11) compressing the UHMWPE seal (29) against the shoulder (31) of the drive casing (11). Additionally, a chamfer at the base of the shaft cover (13) thread locks against a corresponding chamfer on the drive casing (11).

The extension shaft (9) threads onto the drive shaft (7). Rotation of the extension shaft (9) within the shaft cover (13) is prevented by screws (33) in the shaft cover (13) which locate within a longitudinally extending groove (35) on the extension shaft (9). Rotary motion of the drive shaft (7) is thus converted into linear motion of the extension shaft (9).

The end (37) of the extension shaft (9) extending from the shaft cover (13) is radially enlarged and has a screw threaded, axially extending socket (39) therein.

A screw threaded plug (40) secures in the free end (42) of the drive casing (11) to seal the drive (5) therein. At least the housing (3), extension shaft (9) and plug (40) are made of biocompatible material such as titanium.

The end (37) of the extension shaft (9) is securable to a bone with the plug (40) typically being secured to a prosthetic joint such that the endoprosthesis acts as a prosthetic replacement for removed bone.

Figure 3:
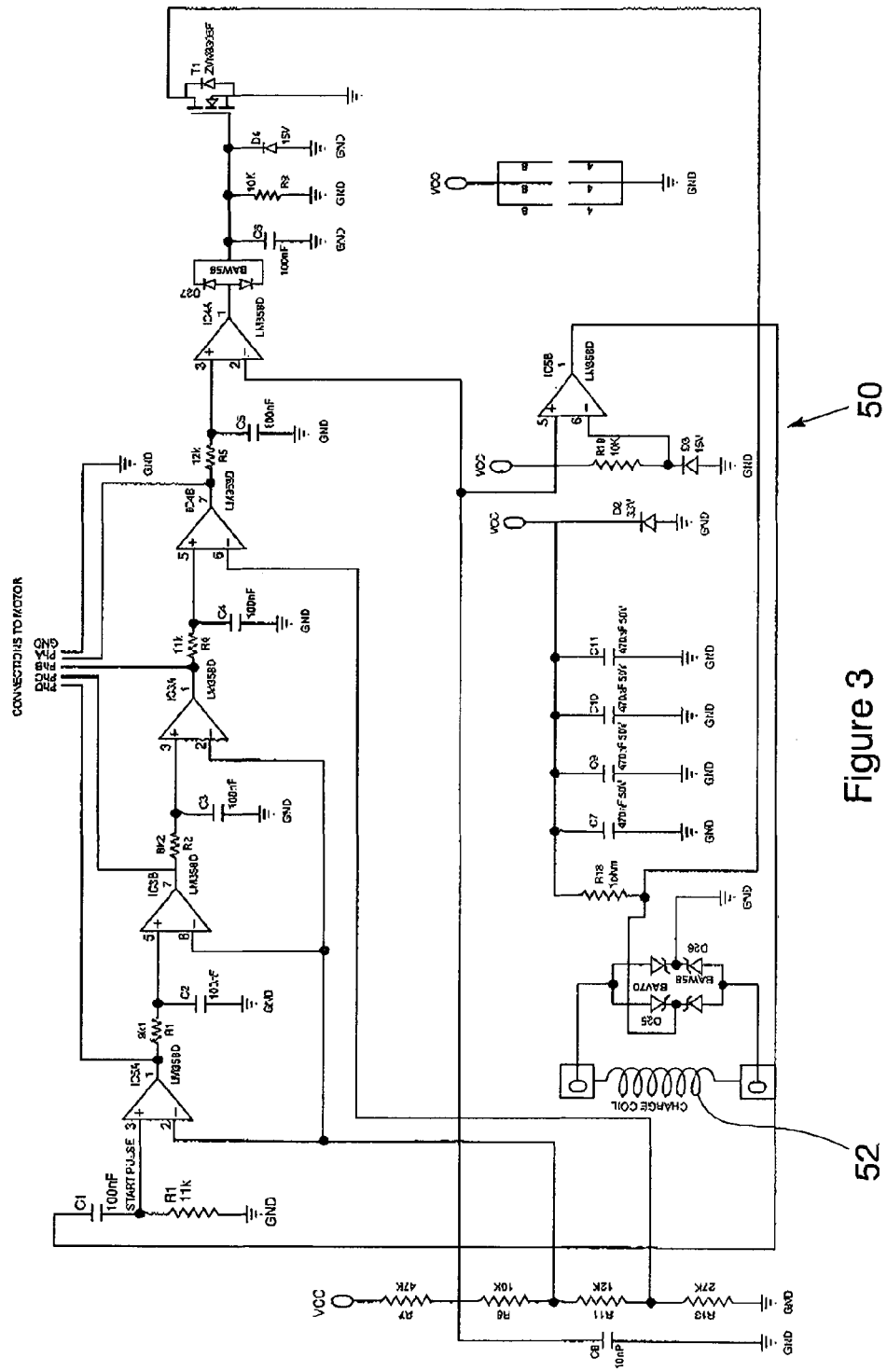
FIG. 3 is a circuit diagram of the control circuit of the endoprosthesis in FIG. 1.

A control circuit (50) is provided within the drive casing (11) intermediate the plug (40) and motor (15). Referring also to FIG. 3, the control circuit (50) includes an inductive coil (52) and a hardwired circuit. The inductive coil (52) is used to supply energy to the system and is a coil of copper wire implanted just under the recipient's skin. The coil connects to D25 and D26 which convert the alternating current from the coil to direct current. C7, C9, C10 and C11 store this energy briefly for use by the circuit. R18 and D2 regulate the voltage supplied to the rest of the circuit.

IC5B, R19 and D3 detect when the power supply has reached a high enough voltage to successfully turn the motor. When this occurs a voltage pulse appears at the point labelled "start-pulse". Four cascaded circuits following the start pulse signal are each a time delay. Each time delay starts the following time delay and each time delay circuit's output drives one phase of the motor.

IC4A is a delay circuit which causes the transistor T2 to conduct, which draws a current impulse from the charge coil. In so doing it discharges the voltage storage capacitors C7, C9, C10, and C11. When these capacitors recharge after the current impulse they cause the entire process to restart. Thus the waveforms above are reproduced for as long as the charge coil is exposed to a suitable alternating magnetic field.

The control circuit is thus configured, in this embodiment through hardwiring, to provide a predetermined output upon receiving power through the inductive coil, and this output causes operation of the motor in a step-wise fashion.

By virtue of the fact that operation of this circuit is hardwired rather than being controlled by a program there is no need for radiation-intolerant memory devices.

Figure 4:
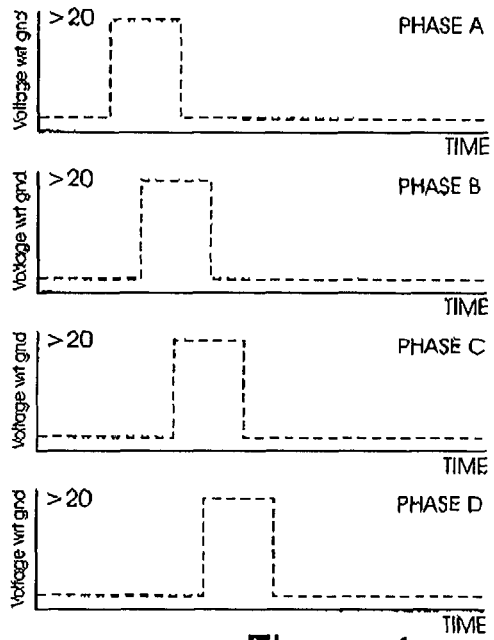
FIG. 4 illustrates the electrical signals required for rotation of the motor of the endoprosthesis in FIG. 1.
Figure 5:
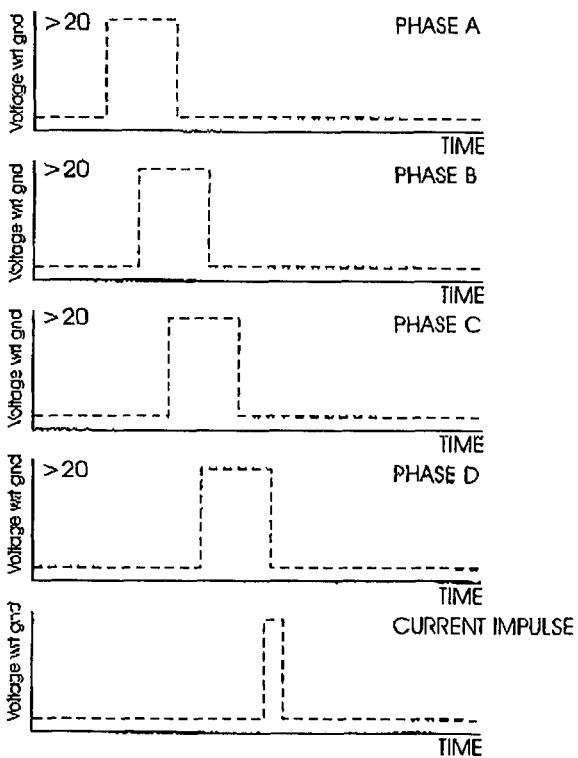
FIG. 5 illustrates the electrical signals in FIG. 4 and the phasing of a control impulse.

The signals from the control circuit (50) required by the motor (15) to make it work are shown in FIG. 4. These waveforms are supplied repeatedly to the motor (15) to rotate it in step-wise fashion. In addition it is very useful to have feedback to measure the rotation of the motor (15) and this is done by drawing a current impulse from the motor drive's power supply. This impulse is phased as shown in FIG. 5.

The energy to drive the system is supplied inductively from outside the body. According to the principles of electrical transformers drawing a current impulse from the power supply within the body will cause a similar current impulse to be drawn from the unit outside the body. Thus by monitoring the current consumption of the external unit it is possible to determine when the motor has taken four "steps" of rotation.

Causing step-wise rotation of the motor thus permits a discrete and known amount of rotation, and hence extension, to be obtained. It also permits control to be simplified through measurement of feedback, obviating the need for sensors to measure rotation or extension.

Should in-vivo force measurements be required, this system could be enhanced by measuring the force experienced by the titanium components by attaching strain gauges to a part which experiences extension force and measuring the strain (fractional compression) of that part. This information could be transmitted out through the skin either using conventional radio techniques (with power supplied through the charge coil) or by using coded patterns of current impulses in an enhancement of the scheme shown in FIGS. 4 and 5.

Figure 6:
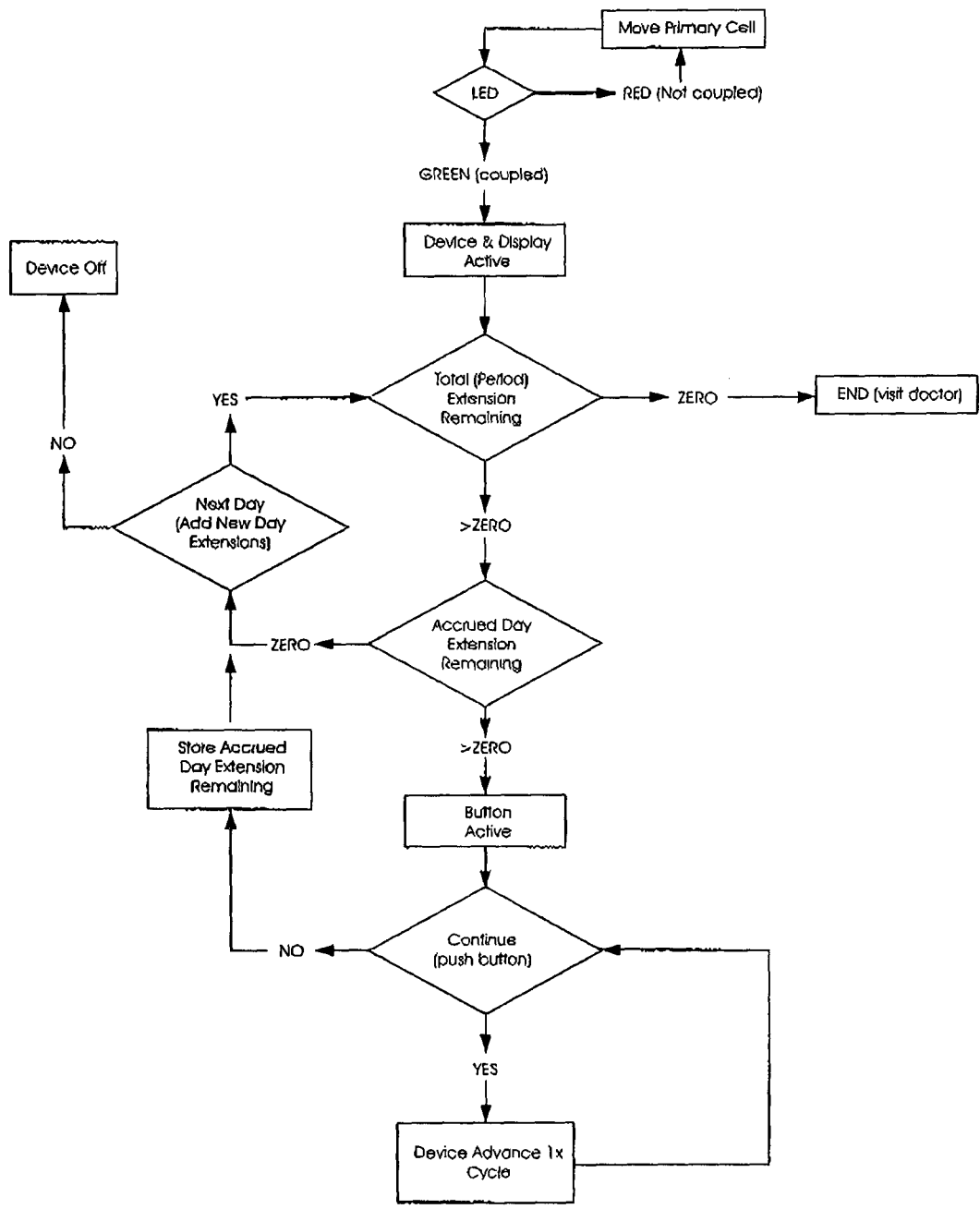
FIG. 6 is flow chart of the control procedure of the endoprosthesis in FIG. 1.

The endoprosthesis (1) thus far described is highly radiation tolerant, and sufficiently radiation tolerant to endure conventional radiation sterilisation An external operating unit (not shown) is also provided which, in this embodiment, straps onto the patient (not shown) so that it can supply an alternating magnetic field to the internal inductive coil (52). In addition it will measure the number of steps taken by the motor (15) and ensure that the motor rotates the correct number of times in a given period. Because this unit is not implanted in the patient there is no need for it to be radiation tolerant. A flow chart of the device control is shown in FIG. 6.

Figure 7:
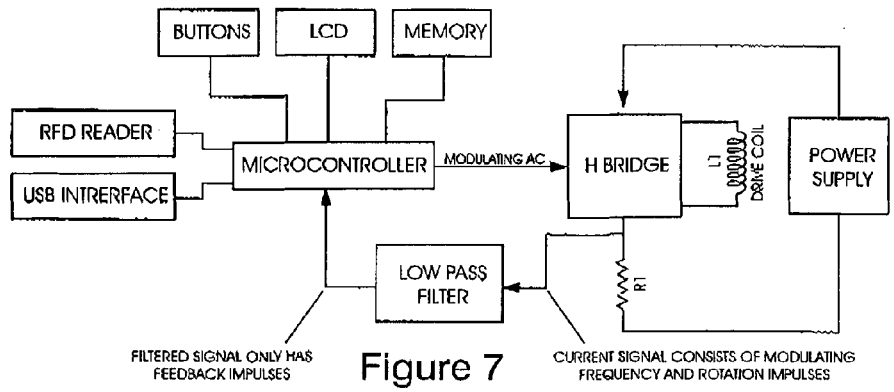
FIG. 7 is a block diagram of the circuit of an external operating device for the endoprosthesis in FIG. 1.

Referring also to FIG. 7, the external operating unit is controlled by a processor, in this embodiment a microcontroller, which can be connected to a computer through an interface, typically USB. When the device is connected to the computer it will be informed, via the interface, of the required extension parameters and will store these in a memory device.

An RFID reader may optionally be present and this would be used to identify that the correct external operating unit, or device, is being applied to the correct endoprosthetic device. To this end an RFID tag (not shown) is associated with the endoprosthesis and may be secured under the skin with the inductive coil or secured to the endoprosthesis. An LCD and buttons may be present for the user to start and stop extension (within the set extension parameters) and to inform the user of the progress of the extension.

The drive coil needs to be driven with an alternating current at high frequency. The charge coil produces an output proportional to rate of change of magnetic field strength, and thus the need for alternating current, with higher coupling efficiencies obtained with increasing drive frequency. The H-bridge is a set of four power switches (typically transistors) which are controlled by the microcontroller to produce this waveform. The resistor, R1 is in series with the power supply to the H-bridge. Current drawn from the H-bridge produces a proportional voltage across the resistor. This voltage has two main sets of frequency components. The first of these is at the drive frequency (and its harmonics) and the second is the reflected current from the current impulses. These signals may be distinguished by their frequency. The reflected impulses will be below 1 kHz (as governed by the operation of the motor) whereas the drive frequency will typically be selected to be in the 100 kHz to 1 MHz region. The low pass filter removes higher frequencies and thus outputs a signal which the microcontroller can use to count the number of steps that the motor has taken. This is then controlled according to the flowchart in FIG. 6 to produce the desired extension.

Thus, by using feedback from the inductive coil, such feedback being received from analysis of the current through or voltage across the inductive coil, operation of the motor is controlled. Extension control is thus effected by the external operating unit and not by the control circuit of the endoprosthesis. This effectively eliminates the need for a programmable microcontroller, or other processor, to be component of the endoprosthesis and also eliminates the need for interaction by the microcontroller or other processor with sensors on the endoprosthesis to control extension thereof. The endoprosthesis is thus relatively simple, robust and highly reliable and not subject to limitations on the method of sterilisation which may be employed.

Figure 8:
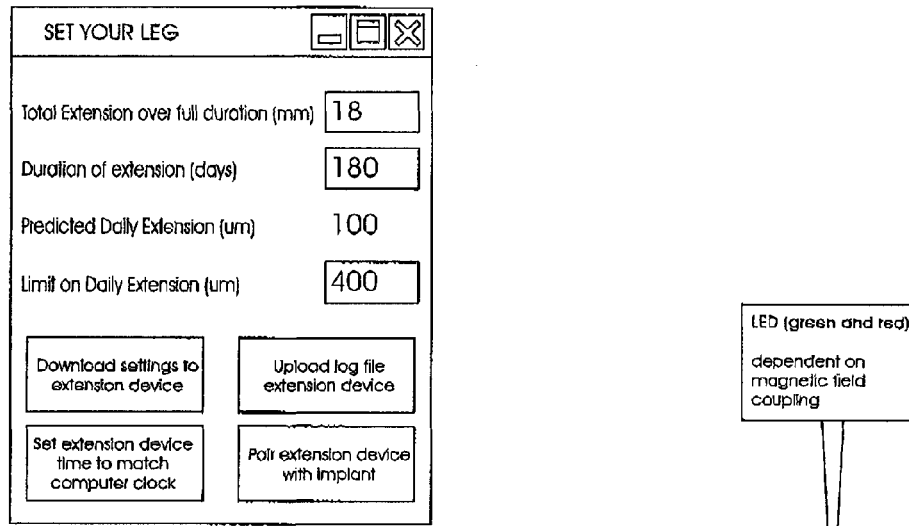
FIG. 8 is an illustration of part of a software interface for the external operating device in FIG. 7.

Medical personnel will need to instruct the external device as to the amount of extension required, and the time profile over which that extension is applied. This is done through a computer based application. An example of the user interface for such a program is shown in FIG. 8. Once the extension information has been entered the settings are downloaded through USB or some similar interface into the external unit.

Figure 9:
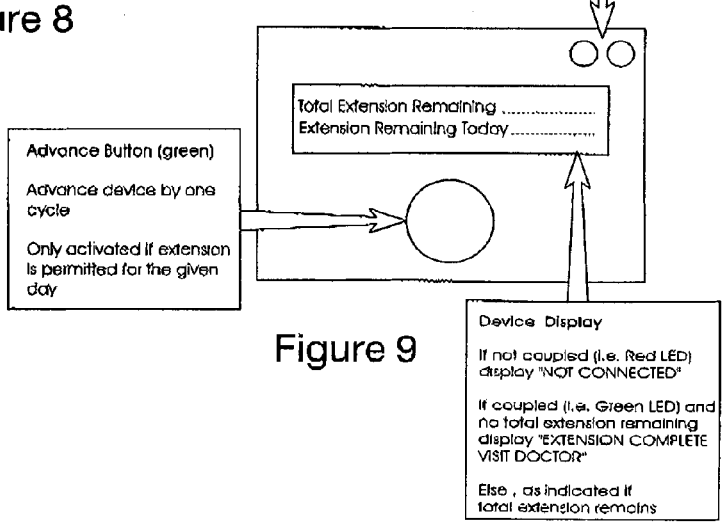
FIG. 9 is a schematic illustration of a patient interface device.

Referring to FIG. 9, the patient interface with the device, having previously been programmed by a specialist, will only have an advance button to the patient to ensure safety. The patient will operate the endoprosthesis the required number of times daily to cause a controlled amount of extension by simply pressing the advance button.

The external device can also be connected to a computer to download operating information to the computer. This may include information such as frequency and time of use by the patient which can be used to determine patient compliance. It may further include measurements made by any strain gauges or other sensors on the endoprosthesis. These measurements could in turn be used to adjust the extension parameters. For example, the measurements may show too little or too much distraction force being applied in which case extensions could be increased or decreased respectively.

The endoprosthesis of the invention is compact, can provide a lengthening force of 2000 N and can be operated externally of the patient. Importantly it can be subjected to radiation without the possibility of damage. This permits it to be effectively sterilised and also permits any suitable form of imaging to be used on the patient once it has been implanted. It will be appreciated, however, that many other embodiments exist which fall within the scope of the invention particularly as with respect to the configuration and control thereof. For example, a stepper motor could be used in place of a piezoelectric motor and the control circuit could make use of any suitable components. Although preferable that it be hardwired, the control circuit need not necessarily be hardwired and could make use of processor, such as a microcontroller, configured to provide a predetermined output.

The invention claimed is:

1. An endoprosthesis comprising an elongate housing having a drive secured through a threaded drive shaft to an extension shaft therein, the drive operable to cause the extension shaft to move axially with respect to the housing and the extension shaft and housing configured to be securable to a bone to act as a prosthetic replacement for removed bone, and for the drive to be operable through a control circuit which includes an inductive coil, wherein the control circuit is configured to provide a predetermined output which operates the drive in a step-wise fashion upon receiving power through the inductive coil and includes a number of cascaded circuits, each of which provides an output which drives one phase of the motor.

2. An endoprosthesis as claimed in claim 1 in which the control circuit is configured through hardwiring.

3. An endoprosthesis as claimed in claim 1 in which the drive includes a motor and gearbox.

4. An endoprosthesis as claimed in claim 3 in which the motor is a piezoelectric motor.

5. An endoprosthesis as claimed in claim 1 in which the cascaded circuits each include a time delay.

6. An endoprosthesis as claimed in claim 1 in which the drive, drive shaft and extension shaft are substantially co-axially arranged.

7. An endoprosthesis as claimed in claim 1 in which a strain gauge is secured to a part of the endoprosthesis to measure strain of that part.

8. An endoprosthesis as claimed in claim 7 in which the strain gauge transmits strain information through the skin using radio techniques or by using coded patterns of current impulses through the inductive coil.

* * * * *